(12) United States Patent
Martens, III

(10) Patent No.: US 7,469,842 B2
(45) Date of Patent: Dec. 30, 2008

(54) VOLATILE DISPENSER WITH ORIENTED FIBROUS EMANATOR

(75) Inventor: Edward J. Martens, III, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/809,027

(22) Filed: May 31, 2007

(65) Prior Publication Data
US 2007/0235552 A1    Oct. 11, 2007

Related U.S. Application Data

(62) Division of application No. 10/880,130, filed on Jun. 29, 2004, now Pat. No. 7,252,244.

(51) Int. Cl.
*A61L 9/04* (2006.01)
*A61L 9/12* (2006.01)

(52) U.S. Cl. .............. 239/44; 239/34; 239/47; 239/145

(58) Field of Classification Search .......... 239/34, 239/44, 45, 47–50, 53, 145, 326
See application file for complete search history.

(56) References Cited

U.S. PATENT DOCUMENTS

| | | |
|---|---|---|
| 3,587,968 A | 6/1971 | Hennert et al. |
| 4,286,754 A | 9/1981 | Jones |
| 4,293,095 A | 10/1981 | Hamilton et al. |
| 4,419,326 A | 12/1983 | Santini |
| 4,739,928 A | 4/1988 | O'Neil |
| 4,753,389 A | 6/1988 | Davis |
| 4,874,129 A | 10/1989 | DiSapia et al. |
| 4,898,328 A | 2/1990 | Fox |
| 4,913,350 A | 4/1990 | Purzycki |
| 4,915,301 A | 4/1990 | Monteahu |
| 5,081,104 A | 1/1992 | Orson, Sr. |
| 5,094,025 A | 3/1992 | Daniels |
| 5,242,111 A | 9/1993 | Nakoneczny et al. |
| 5,497,942 A | 3/1996 | Zingle et al. |
| 5,716,000 A | 2/1998 | Fox |
| 5,840,246 A | 11/1998 | Hammons et al. |
| 5,857,620 A | 1/1999 | Nakoneczny |
| 6,378,780 B1 | 4/2002 | Martens, III et al. |

(Continued)

FOREIGN PATENT DOCUMENTS

EP    0 669 137    8/1995

(Continued)

OTHER PUBLICATIONS

Int'l. Search Report and Written Opinion dated Nov. 8, 2005, Appl. No. PCT/US2005/023037.

(Continued)

*Primary Examiner*—Darren W Gorman

(57) ABSTRACT

A volatile dispenser is provided, including a reservoir containing a quantity of volatile liquid having a viscosity of no greater than 3.9 centipoises. Each of its individual components has a vapor pressure of no less than 0.008 mm Hg. The dispenser also includes an emanator fluidly coupled to the reservoir (either directly or through a wick) that is comprised of elongated oriented bonded fibers, the fibers being impermeable to the volatile material.

15 Claims, 3 Drawing Sheets

U.S. PATENT DOCUMENTS

| | | |
|---|---|---|
| 6,386,462 B1 | 5/2002 | Martens, III |
| 6,435,423 B2 | 8/2002 | Hurry et al. |
| 6,569,152 B2 | 5/2003 | Brines et al. |
| 2001/0030243 A1 | 10/2001 | Hurry et al. |
| 2001/0039414 A1 | 11/2001 | Brtines et al. |
| 2001/0053283 A1* | 12/2001 | Levine et al. ............... 392/395 |
| 2002/0136886 A1* | 9/2002 | He et al. .................. 428/313.5 |
| 2003/0146292 A1 | 8/2003 | Schramm et al. |
| 2003/0168520 A1 | 9/2003 | Triplett et al. |
| 2003/0176853 A1 | 9/2003 | Brines et al. |
| 2004/0060997 A1 | 4/2004 | Jones |
| 2004/0149833 A1 | 8/2004 | Donnelley et al. |

FOREIGN PATENT DOCUMENTS

| | | |
|---|---|---|
| EP | 1 430 958 | 6/2004 |

OTHER PUBLICATIONS

Non-Final Office Action, U.S. Appl. No. 10/880,130 dated Nov. 24, 2006.

* cited by examiner

VOLATILE DISPENSER WITH ORIENTED FIBROUS EMANATOR

CROSS-REFERENCE TO RELATED APPLICATIONS

This application is a divisional application of U.S. patent application Ser. No. 10/880,130, filed Jun. 29, 2004, now U.S. Pat. No. 7,252,244 which is hereby incorporated herein by reference in its entirety.

REFERENCE REGARDING FEDERALLY SPONSORED RESEARCH OR DEVELOPMENT

Not applicable

SEQUENTIAL LISTING

Not applicable

BACKGROUND

1. Field of the Invention

The present invention generally relates to volatile dispensers. More particularly, it relates to liquid volatile dispensers having bonded fibrous emanators.

2. Background of the Invention

A common system for dispensing volatile materials such as perfumes or fragrances includes an impermeable reservoir containing a liquid mixture of the volatile materials. This reservoir has a narrow opening that supports a wick. The wick is inserted through the opening in the reservoir until one end of the wick contacts the liquid in the reservoir and the other end extends outside the reservoir into the surrounding atmosphere.

In operation, the liquid is absorbed by the fibers of the wick and is drawn upward through the wick fibers by microscopic capillary action. The liquid passes up the wick, through the wick opening in the reservoir and wets that portion of the wick that is outside the reservoir.

Since the surrounding atmosphere has a lower partial pressure (i.e. concentration) of volatile materials than the vapor inside the reservoir, the liquid evaporates from the wick outside the reservoir. As it evaporates, the microscopic capillary action causes additional liquid to be drawn up the wick to replace the evaporated liquid, thereby continuing the process of evaporation.

This reservoir and wick arrangement is not necessary to volatilize the liquid, however. An open pan or tray with a large surface area containing a quantity of the liquid would certainly evaporate the liquid material and do so at a much faster rate.

In most applications, however, the goal is not merely to evaporate the volatile liquid, but to evaporate the liquid in a controlled and linear manner over an extended period of time. This is the case with household fragrances. Most consumers would prefer to buy a volatile fragrance dispenser, place it in an area to be scented, and have that area scented at a constant level over an extended period of time, typically, on the order of days, weeks, or even months. For many consumers it is irritating when a volatile scent dispenser provides an overwhelming scent for the first few hours or days, then rapidly fades away to the merest suggestion of the original scent.

For this reason, a longstanding concern and key design goal for the volatile dispensing industry has been to devise volatile dispensers that generate longer lasting scents (in the case of scent dispensers), at a sufficient evaporation rate that are more evenly (linearly) dispensed over an extended period of time.

In order to be transported up a wick, a liquid must have a lower surface tension than the surface energy of the wick to permit the wick fibers to be wetted, and a low viscosity to permit the liquid to be transported through the fibers that comprise the wick via microscopic capillary action.

As a result, the volatile liquids used in volatile dispensers are typically mixtures of several other liquid components in addition to the active ingredient or ingredients that one wishes to dispense. Each additional component serves a specific function, either to increase volatility, to decrease viscosity, or to reduce the surface tension of the volatile liquid.

These additional liquid components collectively act as carriers to lift the active ingredient or ingredients from the surface of the liquid in the reservoir and up through the wick.

There are significant problems using these mixtures. The problems arise because the mixtures are just that—mixtures—and do not stay perfectly mixed as they evaporate. The carriers tend to evaporate sooner and at a faster rate than the dispensed liquid itself. While they do help carry the dispensed liquid up the wick, the carrier fluids tend to evaporate sooner. As a result, they leave significant amounts of the dispensed liquid within the wick itself and significant deposits on the end of the wick.

Over time, as the carrier is preferentially evaporated from the wick, the wick itself is increasingly filled with higher and higher concentrations of the dispensed liquid. This reduces the transport of both the carrier and the dispensed liquid and eventually causes the liquid transport up the wick to cease altogether.

As a result, the effective evaporation rate of volatile dispensers can drop by a factor of fifty percent or more over the emptying lifetime of a typical volatile dispenser. In sum, while the carriers can assist the transport of dispensed liquid, they still do not provide the linearity of dispensing that is desired.

What is needed, therefore, is and improved volatile material dispenser or volatizer that provides a more linear evaporation response. What is also needed is a volatile dispenser that reduces or eliminates the effect of selective evaporation. What is also needed is a volatile dispenser that provides an effective evaporation rate of dispensed material in a package that is small enough to be useable in and around the house.

It is an object of the present invention to provide such a dispenser.

SUMMARY OF THE INVENTION

The present invention substantially overcomes the problem of emanator clogging. By reducing clogging it also enhances linear vaporization of its contained volatile liquid.

The invention is based on the inventor's discovery during development of U.S. Pat. No. 6,378,780 that the non-linearity of vaporization was due primarily to clogging of the liquid transport elements (primarily wicks and emanators) in vaporizing dispensers, and further that this clogging was due to wide variations in the viscosities and vaporization pressures of the individual components.

When the vapor pressures of the individual components are at least 0.008 mm Hg, the inventor discovered that the selective evaporation of individual components is significantly reduced.

Emanators with fine capillary passages can be used to vaporize a volatile fluid in which most of the components have a vapor pressure of no less than 0.008 mm Hg and a low viscosity. Emanators with fine internal capillaries can be fashioned quite thin and broad, with a high surface area to volume ratio, without running the risk of plugged passageways and a blocked emanator.

The present invention also overcomes the need for a large emanator, since the lack of clogging and the effective fluid transport to the surface using the disclosed bonded fiber emanator provides a large effective surface area over the entire several week life of a typically disposable volatile dispenser.

In accordance with a first aspect of the invention, a volatile liquid dispenser is provided, including an impermeable reservoir containing a volatile liquid to be dispensed, a wick in fluid communication with the liquid; and an emanator in fluid communication with the wick, wherein the volatile liquid has a viscosity of no more than about 3.9 centipoises and further wherein the emanator is comprised of bonded, oriented, non-porous fibers.

The fibers may include polyester fibers with a coating of high density polyethylene. The fibers may be bonded together by thermal fusion. The volatile liquid may have a viscosity of no more than about 2.5 centipoises.

An active ingredient of the volatile liquid may be a scent, an insecticide, an attractant, a repellant, a sanitizer, a cleanser, an aromatherapeutic agent and a medicinal. At least 95% by weight of all the components comprising the volatile liquid may have vapor pressures of no less than about 0.008 mm Hg at 20 degrees centigrade. All components of the volatile liquid may have a vapor pressure of no less than about 0.008 mm Hg at 20 degrees centigrade. The emanator may have a thickness in a first direction orthogonal to the longitudinal extent of the fibers of no more than 3.5 mm, and a width in a second direction orthogonal to both the first direction and the longitudinal extent of no less than 10 mm. The fibers may be polyester, polypropylene, nylon, low density polyethylene and high density polyethylene.

In accordance with a second aspect of the invention, a volatile liquid dispenser, is provided, including an impermeable reservoir containing a volatile liquid to be dispensed, and an emanator having a first end and a second end, the first end being in fluid communication with the liquid in the reservoir and the second end being disposed outside the reservoir; wherein the volatile liquid has a viscosity of no more than about 3.9 centipoises and further wherein the emanator is comprised of bonded, oriented, non-porous fibers.

The fibers may be polyester fibers that are coated with high density polyethylene. The fibers may be polyester fibers, high density polyethylene fibers, polypropylene fibers, nylon fibers and low density polyethylene fibers. The volatile liquid may have a viscosity of no more than about 2.5 centipoises. The volatile liquid may be a scent, an insecticide, an attractant, a repellant, a sanitizer, a cleanser, an aromatherapeutic agent and a medicinal. Ninety-five percent by weight of the individual components that comprise the volatile liquid may have vapor pressures of no less than about 0.008 mm Hg at 20 degrees centigrade. Ninety-five percent by weight of all the components comprising the volatile liquid may have a vapor pressure of no less than about 0.008 mm Hg at 20 degrees centigrade. The emanator may have a thickness in a first direction orthogonal to the longitudinal extent of the fibers of no more than 3.5 mm, and a width in a second direction orthogonal to both the first direction and the longitudinal extent of no less than 10 mm.

In accordance with a third aspect of the invention, a method of dispensing a volatile liquid, is provided, including the steps of providing a volatile liquid that is at least 95% by weight of components each having a vapor pressure of no less than 0.008 mm Hg at 20 degrees centigrade; applying the volatile liquid to an emanator comprised of bonded, oriented, non-porous fibers; and evaporating the volatile liquid from the surface of the emanator.

The bonded, oriented, non-porous fibers may be polyester fibers, high density polyethylene fibers, polypropylene fibers, nylon fibers and low density polyethylene fibers. The liquid dispensed material may have a viscosity of no more than about 3.9 centipoises. The bonded, oriented, non-porous fibers may be comprised essentially of coated polyester fibers that are thermally bonded together.

Numerous other features and advantages of the present invention will become readily apparent from the following detailed description, the accompanying drawings, and the appended claims.

DETAILED DESCRIPTION OF THE PREFERRED EMBODIMENTS

Figure 1:
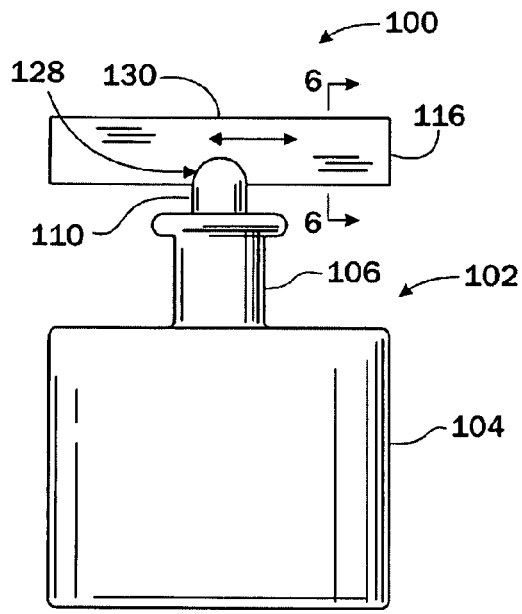
FIG. 1 is a side view of a first volatile dispenser in accordance with the present invention.

While the present invention is susceptible of being made in any of several different forms, the drawings show a particularly preferred form of the invention. One should understand, however, that this is just one of many ways the invention can be made. No particular feature of the illustrated embodiment should be considered a part of the invention, unless that feature is explicitly mentioned in the claims. In the drawings, like reference numerals refer to like parts throughout the several views.

Figure 2:
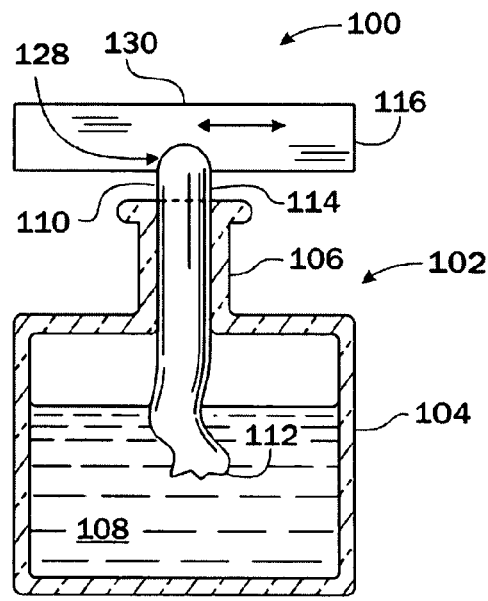
FIG. 2 is a cross sectional side view of the dispenser of FIG. 1.

FIGS. 1 and 2 show a volatile dispenser 100. It includes a reservoir 102 having a generally cylindrical body 104 and a narrow neck 106. Reservoir 102 contains a volatile liquid 108.

A wick 110 has a lower end 112 that is disposed in the liquid 108 and an upper end 114 that extends out of reservoir 102 through neck 106. Upper end 114 is exposed to the surrounding atmosphere.

Figures 5, 6:
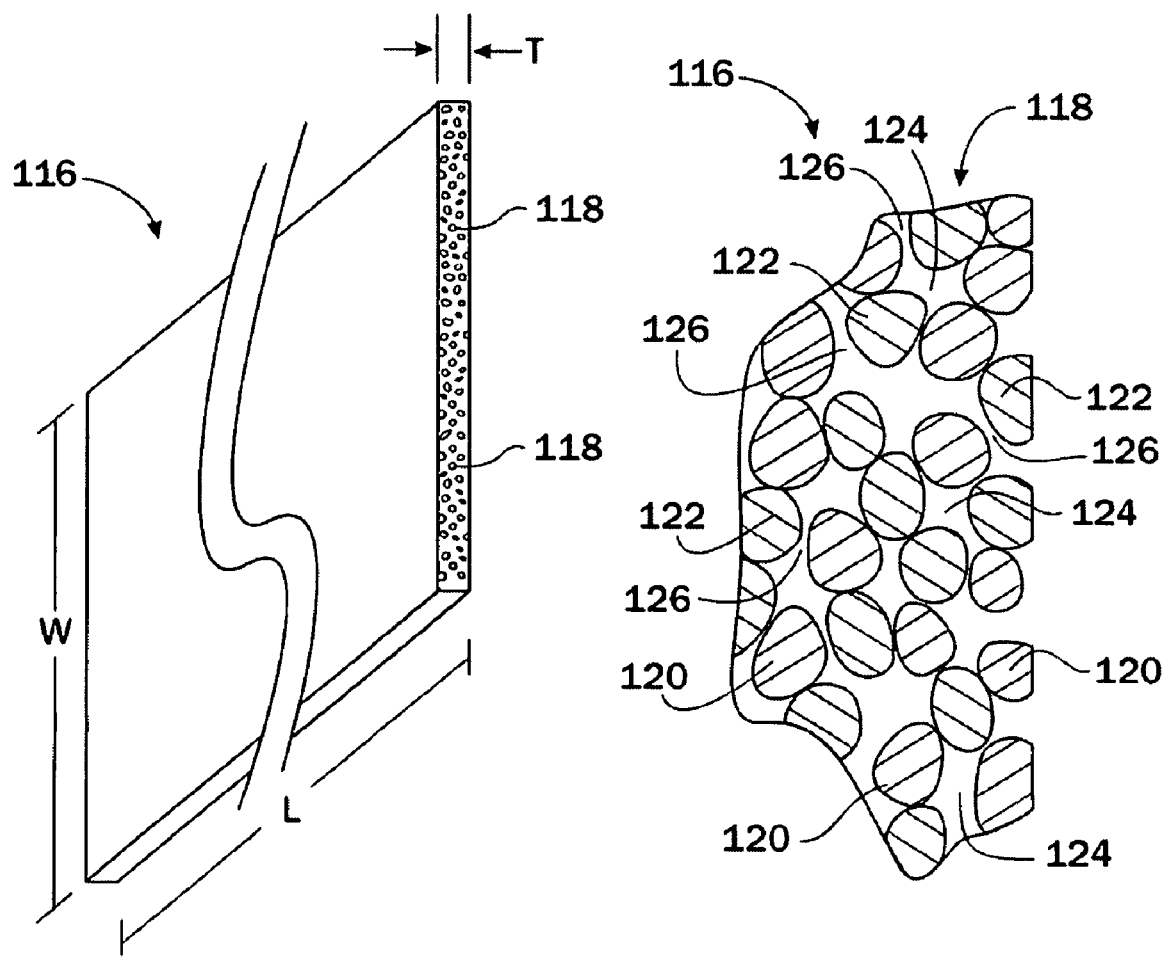
FIG. 5 is a fragmentary cross-sectional view of the emanator of FIGS. 1-4 in a direction normal to the longitudinal extent of the emanator and normal to the individual fibers forming the emanator, wherein the cross section is taken along section line 5-5 in FIG. 1.
FIG. 6 is a fragmentary perspective view of the emanator of FIGS. 1-5.

An emanator 116 abuts and is in fluid communication with end 114 of wick 110. Referring to FIGS. 5 and 6, emanator 116 is comprised of bonded, oriented fibers 118 that are non-porous to the volatile liquid 108 in reservoir 102 and have a diameter of between 0.010 and 0.075 mm; more preferably 0.015 to 0.050; and most preferably 0.018 to 0.025 mm. Fibers 118 are preferably polyester fibers 120 that are intermixed with high density polyethylene fibers 122 and are thermally bonded together. Alternatively, fibers 120 and 122 are all polyester fibers with a coating of high density polyethylene.

In a preferred process for manufacturing the emanator, the coated polyester fibers are made from co-extruding polyester fiber with a coating of polyethylene, drawing them down to a small diameter, gathering them together and drawing them through a heated die that defines the desired emanator dimensions, then permitting them to cool. This process creates a continuous ribbon of emanator having a constant thickness "T" and width "W" that can be cut to any desired length "L".

In the present example, emanator 116 is 2.5 millimeters thick by 12 millimeters wide, by 44 millimeters long. In a preferred embodiment, the thickness of the emanator is preferably between 1 mm and 3.5 mm (preferably no more than 3.5 mm), the width is preferably between 10 and 50 mm (preferably no less than 10 mm), and the length is preferably between 30 and 70 mm.

The heated die for creating this emanator had a die opening (through which the fibers 118 were drawn) that measures 2.5 millimeters by 12 millimeters.

The emanator fibers 118 are bonded to each other in parallel and extend the length of the emanator. This process creates small capillary channels 124 (FIG. 6) that also extend the length of the emanator defined between adjacent groups of fused fibers. These channels 124 are disposed not only on the surface of the emanator 116, but are dispersed throughout the body of emanator 116.

These channels 124 are not sealed over their entire lengths, but have random interconnecting points 126 disposed along their lengths. These interconnecting points provide fluid communication between adjacent channels 124, permitting fluid to pass from one to the other. This communication permits the volatile liquid carried in these channels to be conveyed not just longitudinally (i.e. parallel to the directions the fibers extend) but also laterally.

The interconnections 126 between adjacent capillary channels 124 permit the volatile fluid to be drawn not just lengthwise from one end of the capillary to the other, but also permit sideways flow from one adjacent capillary channel to another across the width of the emanator 116.

The benefits to these interconnections can be seen in FIG. 1. With the cross-capillary flow provided by interconnecting points 126, volatile fluid 108 which first contacts the emanator at the wick/emanator interconnection point 128 travels not only the length of the emanator parallel to the capillaries, but also laterally through the emanator, from one side of the emanator to the other. This flow even reaches point 130 on the edge of the emanator directly opposite the point 128 where the wick feeds the emanator.

The internal capillaries are therefore uniquely suited to transport volatile liquid 108 over the length of the emanator and wet the surface. The capillaries are direct, internal, yet have leakage paths to adjacent capillaries and thence to the surface of the emanator 116, insuring that the entire surface of even a relatively thin emanator, such as emanator 116 is thoroughly wetted.

To further enhance emanator 116 wetting and transport, the emanator is preferably arranged such that the largest dimension of the emanator (its length) runs horizontally and the capillaries created between the fibers run horizontally as well. This encourages the transport of fluid evenly throughout the emanator. Thus, in the embodiment of FIG. 1, the capillaries and fibers extend horizontally.

The illustrated emanator 116 is a flat sheet. Other configurations may be used, however, an emanator may have a different form, e.g. as a tube (preferably round); a cross; an open square and rectangular channel, etc.

Filtrona Richmond, Inc. (1625-A Ashton Park Dr., Colonial Heights, Va. 23834) manufactures a material that is particularly suitable for use as emanator 116. Filtrona calls this material "Filtrona Transorb Wick." A preferred Transorb Wick is identified as model "R-21583".

Volatile liquid 108 is contained in reservoir 102 which provides the supporting structure both for wick 110 and emanator 116. Reservoir 102 is preferably a glass or plastic container that is impermeable to volatile liquid 108.

Volatile liquid 108 includes a fragrance or scent as an active ingredient. In addition to or in place of the fragrance or scent, volatile liquid 108 may include as an active ingredient, an insecticide, an attractant, a repellant, a sanitizer, a cleanser, an aromatherapeutic agent, a medicinal or other fluid that is intended to be vaporized in the atmosphere to take effect.

Volatile liquid 108 may be made of a single active component or ingredient or it may be a mixture of several hundred components or ingredients. The components may include one or more active components and one or more carrier components. The carrier components include components that enhance the vaporization of the one or more active components, or enhance the transport of those components through the wick 110 and emanator 116.

Whether a single active component or a mixture of components, it is desirable that at least 95% by weight of the constituent component fluids that comprise volatile liquid 108 have an individual vapor pressure of no less than 0.008 mm Hg. More preferably, at least 98% by weight of the constituent components have an individual vapor pressure of no less than 0.008 mm Hg. Even more preferably, at least 99% by weight of the constituent components have an individual vapor pressure of no less than 0.008 mm Hg. Most preferably, all of the constituent components have an individual vapor pressure of no less than 0.008 mm Hg.

Volatile liquid 108 preferably has a viscosity of no more than 3.9 centipoises, and more preferably no more than 2.5 centipoises.

Figure 3:
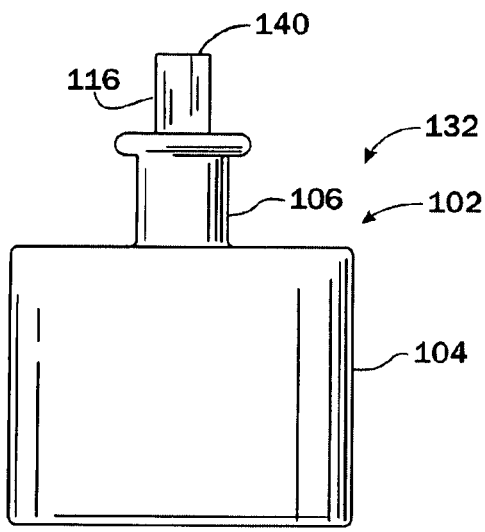
FIG. 3 is a side view of a second volatile dispenser.
Figure 4:
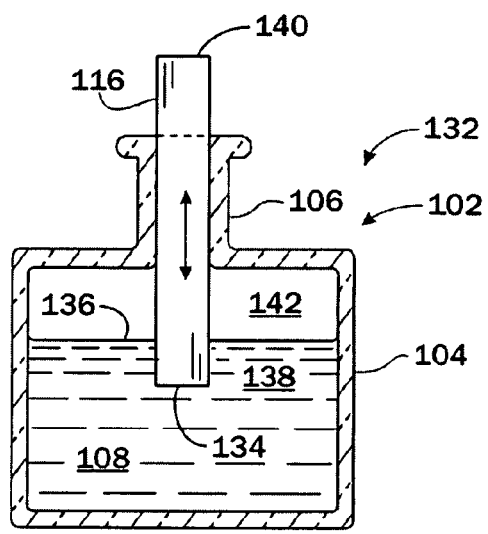
FIG. 4 is a cross sectional side view of the dispenser of FIG. 2.

FIGS. 3 and 4 illustrate an alternative dispenser in which the emanator is in direct contact with the liquid in the reservoir. In this embodiment, a volatile dispenser 132 includes a reservoir 102 having a generally cylindrical body 104 and a narrow neck 106. Reservoir 102 contains volatile liquid 108.

Emanator 116 has a lower end 134 that extends through free surface 136 of a pool 140 of liquid 108. Emanator 116 has an upper end 140 that extends through a vapor-filled region 142 of reservoir 102 through neck 106 and out into the surrounding atmosphere.

The bonded fibers that comprise emanator 116 are oriented vertically in FIGS. 3 and 4, as indicated by the double-headed arrow on emanator 116. One end of each of the fibers of emanator 116 is therefore immersed in volatile fluid 108 and the other end of the fiber is disposed outside of the reservoir in the open air. Similarly, each capillary channel 124 of emanator 116 defined by the fibers is also immersed in fluid 108 at one end and has its opposing end disposed in the surrounding atmosphere.

Figure 7:
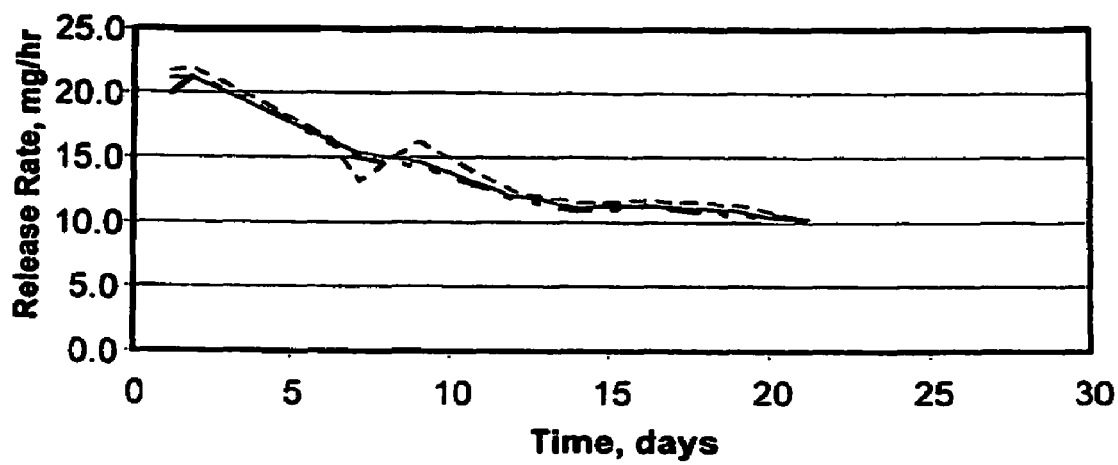
FIG. 7 is a Filtrona prototype chart. Release rate is plotted on the Y-axis in units of mg/hr and time is plotted on the X-axis in units of days.

FIG. 7 illustrates tests conducted on the embodiment of FIGS. 1 and 2. FIG. 7 shows the vaporization curves of three identically configured volatile dispensers 100. The volatile liquid was a fragrance identified in U.S. Pat. No. 6,378,780. Similar fragrances made with components having the specific viscosities and vapor pressures identified herein can be ordered from and formulated by any international fragrance company.

In FIG. 7, the dispenser 100 using emanator 116 begins with a release rate of 21 milligrams per hour (mg/hr), dropping down to a relatively constant rate of between 15 and 10 mg/hr for two weeks.

Figure 8:
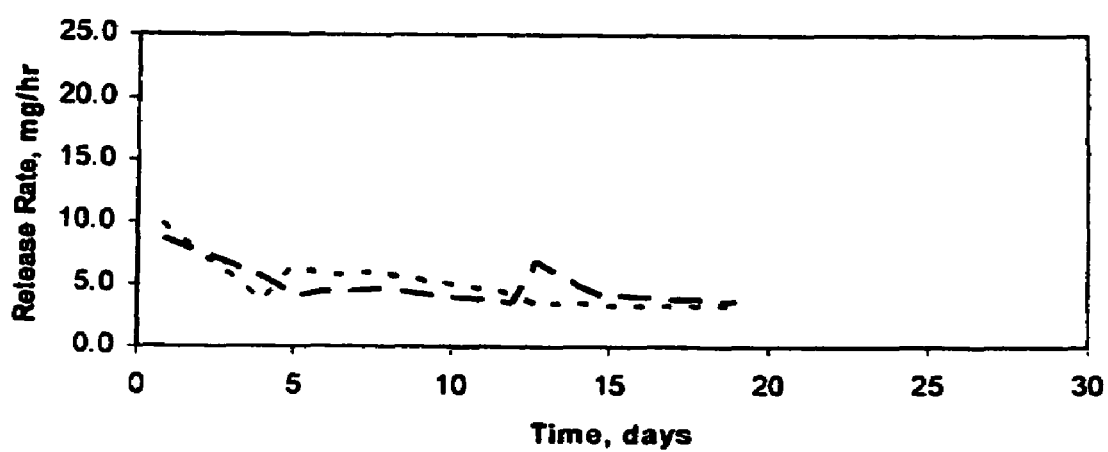
FIG. 8 is a surface capillary chart. Release rate is plotted on the Y-axis in units of mg/hr and time is plotted on the X-axis in units of days.

Compare this rate with the release rate of a similar dispenser illustrated in FIG. 8. The FIG. 8 emanator has a 3 inch square surface area. It is about 50% larger than the FIG. 7 emanator. It has molded surface capillaries, such as those illustrated in U.S. Pat. No. 4,913,340. Using the identical volatile material and reservoir, two vaporization test runs were made using the molded surface capillary emanator. The results are shown below in FIG. 8.

Note that the maximum release rate of the FIG. 8 device is less than half the release rate of the FIG. 7 device (the FIG. 1 device) using emanator 116 even though the FIG. 8 emanator has 50% more surface area.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

INDUSTRIAL APPLICABILITY

A volatile liquid dispenser has a volatile liquid with a low viscosity, made of liquid components each having a high volatility. These characteristics permit the dispenser to be used with a bonded fiber wick having small capillaries without clogging. As a result, the dispenser provides more linear vaporization characteristics.

I claim:

1. A volatile liquid dispenser, comprising:
   an impermeable reservoir containing a volatile liquid to be dispensed; and
   an emanator having a length extending completely between a first end and a second end, the first end being in fluid communication with the liquid in the reservoir and the second end being disposed outside the reservoir;
   wherein the emanator is comprised of bonded, oriented, non-porous fibers, and wherein the emanator has a constant thickness and width along the length thereof.

2. The dispenser of claim 1, wherein the fibers are polyester fibers that are coated with high density polyethylene.

3. The dispenser of claim 1, wherein the fibers comprise polyester, high density polyethylene, polypropylene, nylon, or low density polyethylene.

4. The dispenser of claim 3, wherein the volatile liquid has a viscosity of no more than about 2.5 centipoises.

5. The dispenser of claim 4, wherein the volatile liquid comprises a scent, an insecticide, an attractant, a repellent, a sanitizer, a cleanser, an aromatherapeutic agent, or a medicinal fluid.

6. The dispenser of claim 4, wherein 95% by weight of the individual components that comprise the volatile liquid have vapor pressures of no less than 0.008 mm Hg at 20 degrees centigrade.

7. The dispenser of claim 1. wherein 95% by weight of all the components comprising the volatile liquid have a vapor pressure of no less than 0.008 mm Hg at 20 degrees centigrade.

8. The dispenser of claim 7, wherein the emanator has a thickness of no more than 3.5 mm and a width of no less than 10 mm.

9. A volatile liquid dispenser, comprising:
   a reservoir containing a volatile liquid; and
   an emanator having a length extending between a first end and a second end, the first end being in fluid communication with the liquid in the reservoir and the second end being disposed outside the reservoir,
   wherein the emanator is comprised of non-porous fibers that are thermally bonded together and oriented in parallel with and extend the length of the emanator.

10. The volatile liquid dispenser of claim 9, wherein the volatile liquid has a viscosity of no more than about 3.9 centipoises.

11. The dispenser of claim 9, wherein the volatile liquid comprises a scent, an insecticide, an attractant, a repellant, a sanitizer, a cleanser, en aromatherapeutic agent, or a medicinal fluid.

12. The dispenser of claim 9, wherein 95% by weight of the individual components that comprise the volatile liquid have vapor pressures of no less than 0.008 mm Hg at 20 degrees centigrade.

13. The volatile liquid dispenser of claim 1, wherein the non-porous fibers are thermally bonded together.

14. The volatile dispenser of claim 13, wherein the non-porous fibers are oriented in parallel and extend the length of the emanator.

15. The volatile dispenser of claim 14, wherein the volatile liquid has a viscosity of no more than about 3.9 centipoises.

* * * * *